(12) United States Patent
Gaspard

(10) Patent No.: US 8,142,375 B2
(45) Date of Patent: Mar. 27, 2012

(54) AUTOMATED INFANT MASSAGER

(76) Inventor: Sanna Gaspard, Pittsburgh, PA (US)

( * ) Notice: Subject to any disclaimer, the term of this patent is extended or adjusted under 35 U.S.C. 154(b) by 330 days.

(21) Appl. No.: 12/051,906

(22) Filed: Mar. 20, 2008

(65) Prior Publication Data

US 2008/0242957 A1    Oct. 2, 2008

Related U.S. Application Data

(60) Provisional application No. 60/908,749, filed on Mar. 29, 2007.

(51) Int. Cl.
    *A61B 5/00* (2006.01)

(52) U.S. Cl. ............... 601/84; 600/300; 600/22; 606/1

(58) Field of Classification Search ................. None
    See application file for complete search history.

(56) References Cited

U.S. PATENT DOCUMENTS

| | | | |
|---|---|---|---|
| 3,290,985 A | 12/1966 | Bains et al. | |
| 3,802,420 A * | 4/1974 | Moffat et al. | 601/114 |
| 3,994,290 A | 11/1976 | Springer et al. | |
| 4,088,124 A | 5/1978 | Korner et al. | |
| 4,191,177 A * | 3/1980 | Abbott | 601/97 |
| 4,681,096 A | 7/1987 | Cuervo | |
| 4,754,747 A | 7/1988 | Hasofer | |
| 4,777,945 A | 10/1988 | Curtaz et al. | |
| 4,834,075 A | 5/1989 | Guo et al. | |
| 5,006,105 A * | 4/1991 | Sherard | 600/22 |
| 5,052,377 A | 10/1991 | Frajdenrajch | |
| 5,054,472 A | 10/1991 | Stefan | |
| 5,063,912 A | 11/1991 | Hughes | |
| 5,125,399 A | 6/1992 | Tarjoto | |
| 5,446,934 A | 9/1995 | Frazier | |
| 5,505,691 A | 4/1996 | Fenkell | |
| 5,820,573 A | 10/1998 | Ramos | |
| 5,853,005 A * | 12/1998 | Scanlon | 600/459 |
| 5,951,501 A | 9/1999 | Griner | |
| 6,052,852 A | 4/2000 | Huang | |
| 6,142,963 A | 11/2000 | Black et al. | |
| 6,175,981 B1 | 1/2001 | Lizama et al. | |
| 6,402,709 B1 | 6/2002 | Wu | |

(Continued)

OTHER PUBLICATIONS

Ottenbacher et al., "The Effectiveness of Tactile Stimulation as a Form of Early Intervention: A Quantitative Evaluation", Developmental and Behavioral Pediatrics, Apr. 1987, vol. 8, No. 2, pp. 68-76.

(Continued)

*Primary Examiner* — Sam Yao
*Assistant Examiner* — Lynsey Crandall
(74) *Attorney, Agent, or Firm* — Eckert Seamans Cherin & Mellott, LLC; Arnold B. Silverman

(57) ABSTRACT

An automated infant massager has a base for supporting the infant and a plurality of first movable massage elements structured to underlie a portion of the infant. At least one motor is employed for effecting reciprocating movement of the first movable massage element. A plurality of second movable massage elements is provided for massaging the arms and legs of the infant. A plurality of third movable elements is provided within a head support for massaging portions of the infant's head, and a plurality of fourth movable massage elements are provided for massaging the infant's shoulders. The infant massager may, in one embodiment, be structured to receive and massage a premature infant, and in another embodiment, may be structured to receive and massage a full-term infant.

54 Claims, 18 Drawing Sheets

U.S. PATENT DOCUMENTS

| | | |
|---|---|---|
| 6,409,654 B1 * | 6/2002 | McClain .......................... 600/22 |
| 6,454,731 B1 | 9/2002 | Marcantoni |
| 6,478,755 B2 | 11/2002 | Young |
| 6,814,709 B2 | 11/2004 | Schwartz et al. |
| 7,004,916 B2 | 2/2006 | Dehli |
| 7,175,592 B2 | 2/2007 | Lee |
| 2002/0033628 A1 * | 3/2002 | Clough .......................... 297/410 |
| 2002/0145512 A1 * | 10/2002 | Sleichter et al. ............. 340/407.1 |
| 2003/0212352 A1 | 11/2003 | Kahn |
| 2005/0151401 A1 * | 7/2005 | Evans .......................... 297/250.1 |
| 2006/0036202 A1 * | 2/2006 | Iwata et al. ...................... 601/88 |
| 2006/0069333 A1 | 3/2006 | Pidcock |

OTHER PUBLICATIONS

Tiffany Field et al., "Massage of Preterm Newborns to Improve Growth and Development:", Pediatric Nursing, Nov./Dec. 1987, vol. 13/No. 6, Antony J. Jannetti, Inc. Publication, USA.

D. Acolet et al., "Change in Plasma Cortisol and Catecholamine Concentration Ions in Response to Massage in Preterm Infants", Archives of Disease in Childhood, 1993;68:29-31.

Ottenbacher et al. meta-analysis of 19 stimulation studies.

* cited by examiner

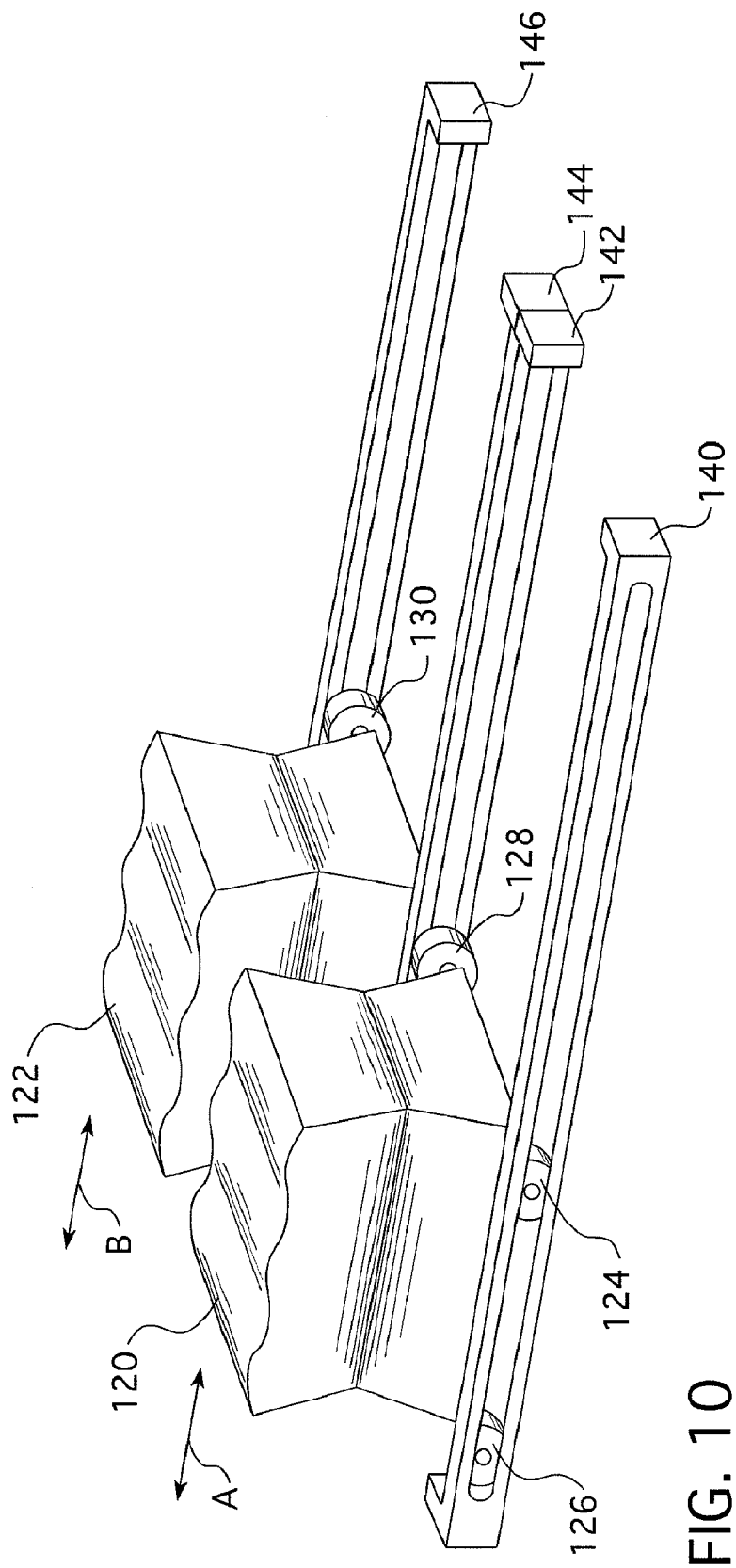

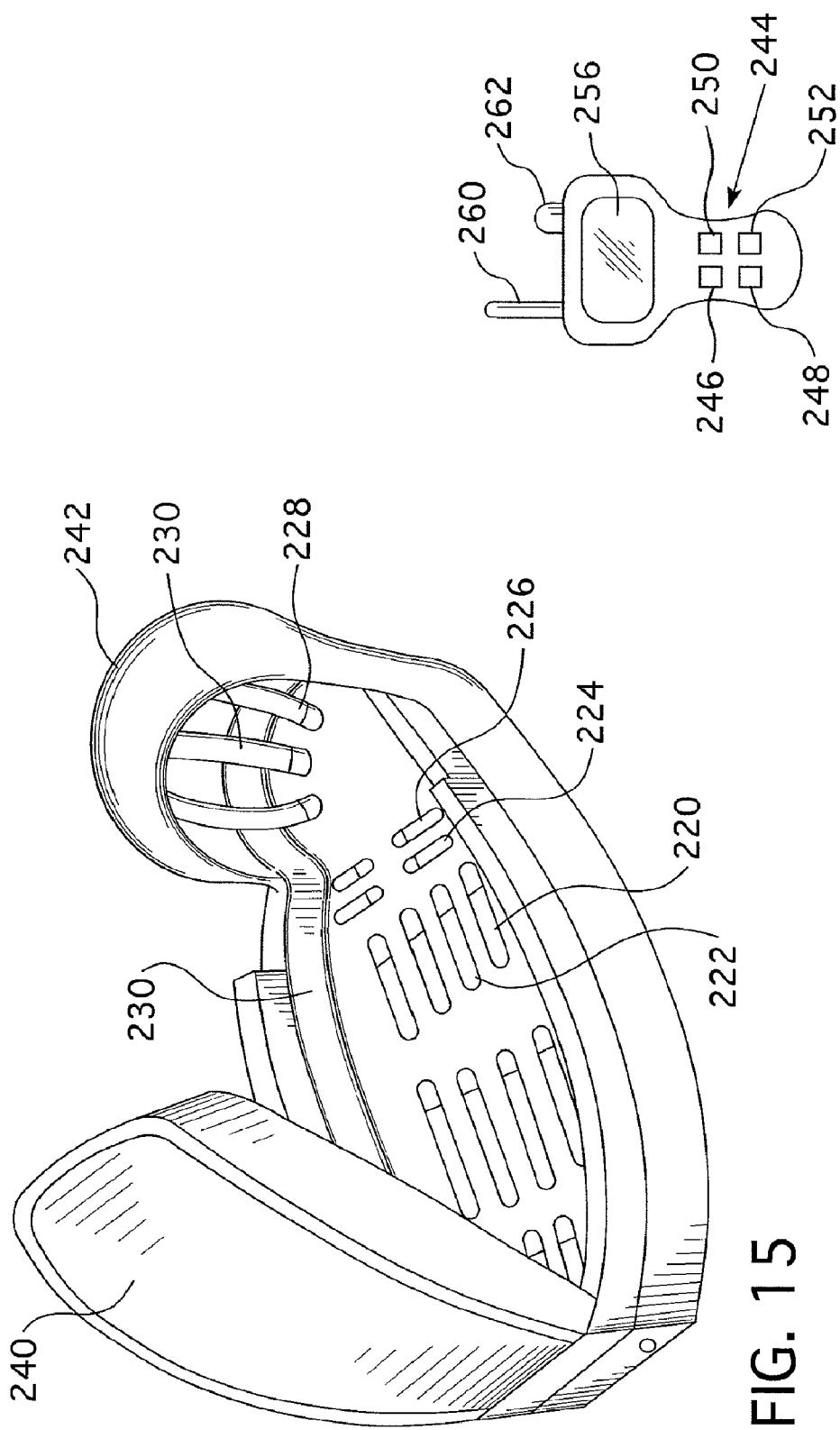

AUTOMATED INFANT MASSAGER

CROSS-REFERENCE TO RELATED APPLICATION

The present application claims the benefit of U.S. Provisional Patent Application Ser. No. 60/908,749, filed Mar. 29, 2007, entitled "Automated Infant Massager," the disclosure of which is expressly incorporated herein by reference.

BACKGROUND OF THE INVENTION

1. Field of the Invention

The present invention relates to an improved, automated infant massager, and more specifically, it relates to such a massager which is structured to be used on premature infants and can be adapted for use with full-term infants.

2. Description of the Prior Art

Hospitals aiming to help highly-compromised premature infants by a range of medical interventions must typically separate these babies from their parents at birth. Usually isolated in incubators that protect them, these preemies receive significantly less touching than full-term babies in the first days and weeks of life. In fact, many intensive care nurseries have, in the past, discouraged any "unnecessary" touching of neonates, in part because some early reports claimed that certain procedures involving handling, e.g., incubation and diaper changes, led to physiological disruptions, such as decreases in oxygen tension. To some extent, the medical community interpreted these reports as cautions against touching neonates in any other-than-essential manner until the 1986 study at TRI by Field et al., which marked a turning point of premature touch therapy protocol. At TRI, Field et al. documented the effects of touch on forty premature infants. The researchers used a basic infant massage consisting of simple body strokes and passive limb movements for three fifteen-minute periods a day for ten days. The study results showed that the preemies who received massage: (1) averaged a 47 percent greater weight gain, even though the groups did not differ in average food intake (in calories or volume) (which increases their survival rate by 30%); (2) were awake and active a greater percentage of the time and (3) exhibited greater alertness, orientation, and responsiveness on the Brazelton Neonatal Behavior Assessment Scale.

Other studies have supported these findings and defeated the "common wisdom" about preterm neonates presumed hyper-responsiveness to touch. Acolet et al. showed, for example, that gentle massage of the head and back of the ICU neonate does not increase the need for oxygen, but in fact, helps the infant cope physiologically with stress. Other studies showed greater weight gain, motor activity and alertness in preterm neonates who did not require intensive care. A meta-analysis by Ottenbacher et al. of 19 stimulation studies illustrated that most preterm infants were positively affected by touch stimulation, typically with greater weight gain and better performance on developmental tests. Follow-up research has suggested that massage has long-term benefits for premature infants. Eight months after being massaged in the neonatal ICU, the stimulated babies continued to gain more weight and perform better on developmental tests than a control group.

Despite the medical benefits of massage, it is time-consuming and requires a trained nurse, which makes its incorporation into the neonatal intensive care unit difficult.

Another reason why infant massage has not been widely implemented is due to the current nursing shortage, which is estimated to reach about one million by the year 2020.

U.S. Pat. No. 4,088,124 discloses an apparatus said to prevent apnea in a premature infant. This is accomplished by placing an infant on a waterbed and establishing controlled flow of fluid oscillations of the fluid of low amplitude and predetermined frequency under the infant.

Additional prior art patents of general interest are as follows:

| Title | U.S. Pat. No. |
|---|---|
| Massaging Device for Chairs with Guide Rail | 7,004,916 |
| Chair Massage | 6,454,731 |
| Cyclically Driven, Straightly and Reciprocally Moving Massage Device | 6,402,709 |
| Massaging Mattress | 6,052,852 |
| Mechanical Massaging Device | 7,175,592 |
| Massaging Bed with Light | 6,814,709 |
| Pulsating Muscle Massaging Device | 5,951,501 |
| Personal Cuddling & Massaging Device | 5,125,399 |
| Treatment of Colic Infants | 4,754,747 |
| Method & Apparatus for Therapeutic Motion and Sound Treatments of Infants | 4,681,096 |
| Electrochemical Massage Apparatus | 4,834,075 |
| Massaging Blanket | 6,142,963 |
| Sleeping Inducing Devices | 5,063,912 |
| Body Contour Massage Device | 5,820,573 |
| Therapeutic Treatments Machine | 5,505,691 |
| Massage Machine | 5,054,472 |
| Apparatus for Massaging the Body by Cyclic Pressure & Constituent | 5,052,377 |
| Punctual Massager Using Vertical Rotary Movements of Massaging Pins | 4,777,945 |
| Massage Device | 3,994,290 |
| Portable Massager | 6,478,755 |
| Method for Treating Premature Infants | 4,088,124 |
| Portable Vibrating Sleep Pad | 6,175,981 |

SUMMARY OF THE INVENTION

The present invention has met the above-described need by providing an automated infant massager which is suitable for use with premature infants, as well as full-term infants. The massager provides a base for supporting the infant and a plurality of first movable massage elements structured to underlie a portion of the infant with at least one motor for effecting reciprocating movement of the plurality of first movable massage elements for massaging the back. The massager also may have a plurality of second movable massager elements for massaging the infant's arms. A head support may be provided for the infant with a plurality of third movable massage elements massaging the infant's head, and a plurality of fourth movable elements may be provided for massaging the infant's shoulders. Various combinations of movable elements may be provided for effecting automated reciprocating massage to various parts of the infant's body. For example, the plurality of first movable massage elements may be employed to massage a portion of the back of the infant's legs in addition to the infant's back.

It is an object of the present invention to provide an automated infant massager is suitable for massaging a premature infant, as well as full-term infants.

It is a further object of the present invention to provide such a massager which may be remotely controlled through a handheld transmitter, for example, or may have direct controls on the massager itself or both.

It is a further object of the present invention to provide such an infant massager which is provided with efficient controls to establish the desired functionality and safety while effectively massaging the infant and to provide alarm indicators in the event of a malfunction.

These and other objects of the present invention will be more fully understood from the following detailed description of the invention and reference to the illustrations appended hereto.

BRIEF DESCRIPTION OF THE DRAWINGS

FIG. 1(a) is a detailed plan view of a portion of the track and massaging elements which move thereon.

FIG. 10 is a schematic illustration of two massaging elements the and associated tracks.

FIG. 15 is a perspective view of an alternate embodiment of a massager of the present invention for use with full-term infants.

FIG. 16 is a view of a remote transmitter for controlling certain functions of operation of the massager in FIG. 15.

DESCRIPTION OF THE PREFERRED EMBODIMENTS

The infant massager will contain a housing unit that will massage the head, back, arms, shoulders, and legs of the infant through a plurality of massage elements. The device will not massage the chest. Each side of the device will have two protrusions that will be used to massage the top surface of the arms and legs. The support surface of the device will be lined with soft materials and boundaries for the infant where needed.

Figure 1:
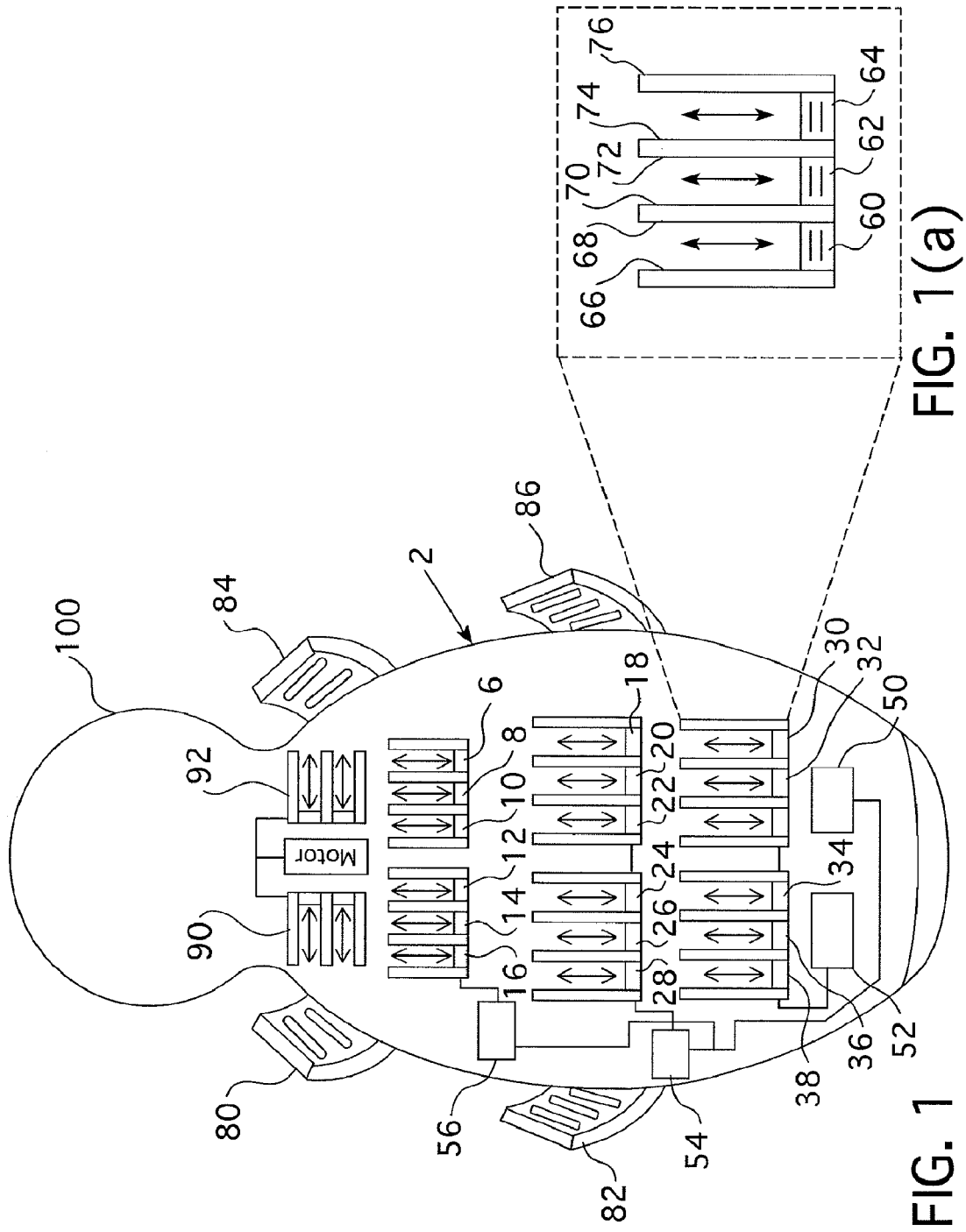
FIG. 1 is a schematic, top plan view of a form of automated infant massager of the present invention.

Referring to FIGS. 1 and 1(a), there is shown an automated infant massager which has a base 2, a plurality of first movable massage elements, such as 6, 8, 10, 12, 14, 16, 18, 20, 22, 24, 26, 28, 30, 32, 34, 36, 38, which in the form shown, are structured to partially support and massage the back of an infant by moving in the reciprocal direction shown by the arrows, which in the form shown, will extend in a direction generally parallel to the infant's spinal column. In the form shown, a battery 50 will serve to energize at least one motor 52. In the specific form shown, motors 54, 56 are operatively associated with the first plurality of massage elements 6-38 (even numbers only). Alternatively, if desired, the massager may be plugged into an electrical outlet and energized in that manner. The transmissions may be of any desired means which, as well known to those skilled in the art, will convert the output of a motor shaft into reciprocating movement of the first plurality of movable massaging elements 6-38 (even numbers only). As shown in FIG. 1(a), movable massage elements 60, 62, 64 are each operatively associated with a pair of parallel tracks, such as (a) 60 and tracks 66, 68; (b) movable massage element 62, with tracks 70, 72; and (c) movable massage element 64 being associated with generally parallel tracks 74, 76. At the lateral sides of the base 2 are a plurality of second massage elements secured on supports 80, 82, 84, 86. Reciprocating movable massage elements 90, 92 in the form shown move in a direction generally transverse to the direction of movement of the adjacent massage elements 6-36 (even numbers only) and are activated by the illustrated motor.

Figure 2:
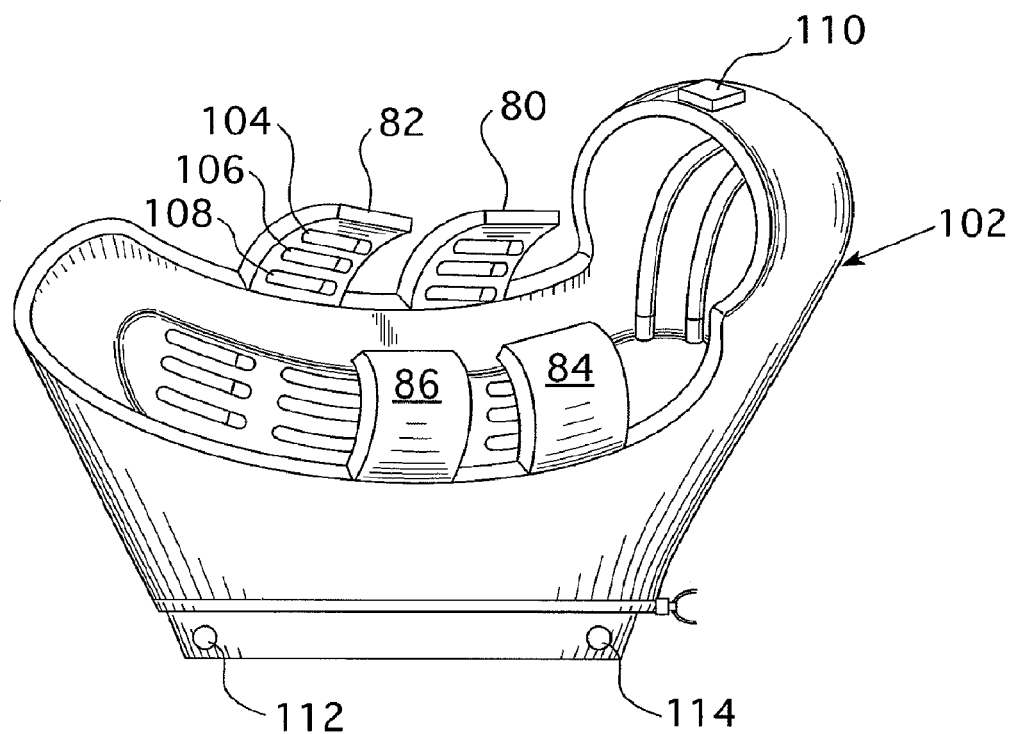
FIG. 2 is a perspective view of a form of the infant massager of the present invention with a cover in place.

FIG. 2 shows the infant massage apparatus of FIG. 1 with the supports 80, 82, 84, 86 in the open position. These each support the plurality of second movable massage elements which will massage portions of the arms and legs of the infant. See, for example, elements 104, 106, 108 of support 82. The boundaries 85 (FIG. 3) preferably will be soft, so as to provide a soft barrier to help keep the infant in position. It also serves to surround the infant to provide boundaries and help the infant feel secure. It also shows the brow monitor 110 which is structured to embrace the head of the infant and indicate through an alarm message or signal if the infant has moved out of a position, wherein the head contacts the brow monitor. FIG. 2 also shows the brow monitor 110 which is in the storage position on top of the cover 102. In use, it is secured to the forehead of the infant by a mild adhesive and serves to provide an indication of the infant wrinkling its brow, which is a known sign of pain or other discomfort. This information will be delivered to the massager transmitter (not shown) for wireless transmission to the handheld unit or other monitoring unit. The brow monitor also serves to monitor head movement of the infant. The brow monitor 110 could also be fixedly secured to the head support. Depending upon the type of movement that is being sensed by the brow monitor 110 in a particular instant, the information wirelessly transmitted to the remote unit could trigger an alarm message or merely signal that the infant has moved out of position such that the head is no longer contacting the monitor. It will be appreciated that the prime function of the brow monitor 110 is to monitor brow movement, blinks, and facial movements to provide meaningful feedback.

Massage unit cover 102 has a plurality of openings through which movable massage elements, such as 104, 106, 108, will pass. FIG. 2 also shows the power input jack connection 112 and monitor jack input 114 for monitoring the performance of the system.

Figure 3:
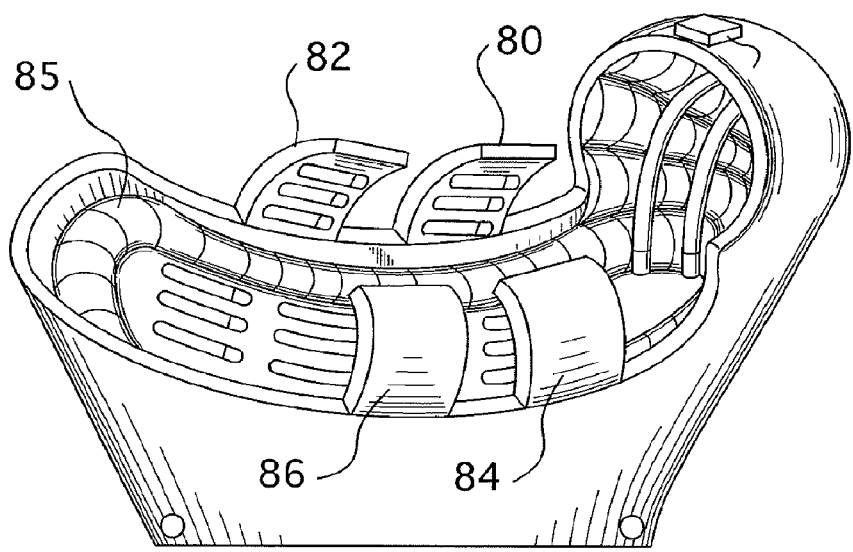
FIG. 3 is a form of infant massager of the present invention with the massager shown in the open position.

FIG. 3 shows the massaging apparatus in the closed position with the boundaries 85 serving to provide padded protection around the circumference of the upwardly-open recess which receives the infant.

Figure 6:
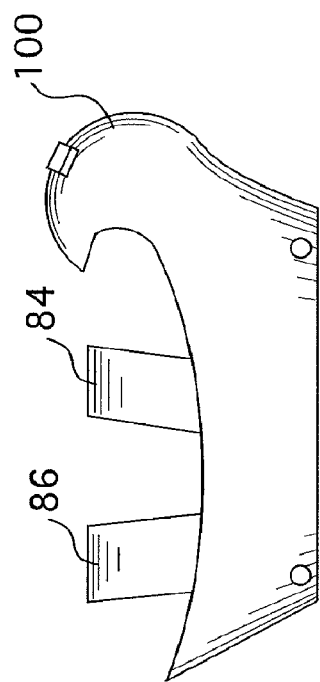
FIG. 6 is a right elevational view of the infant massager of the present invention in the open position.
Figure 4:
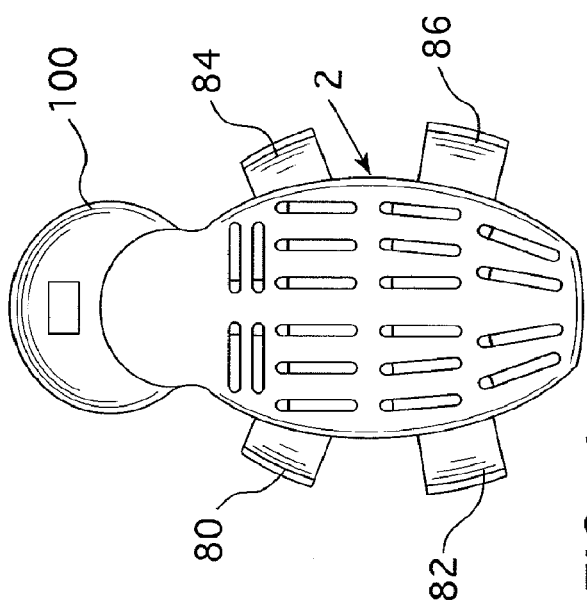
FIG. 4 is a top plan view of the infant massager of FIG. 3 in the open position.
Figure 5:
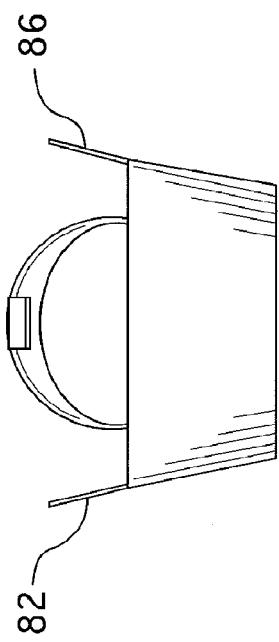
FIG. 5 is a front elevational view of the infant massager of the present invention in the open position.

FIGS. 4 through 6 show, respectively, plan front elevational and right-side elevational views of the massaging device in the open position for use with premature infants.

Figure 9:
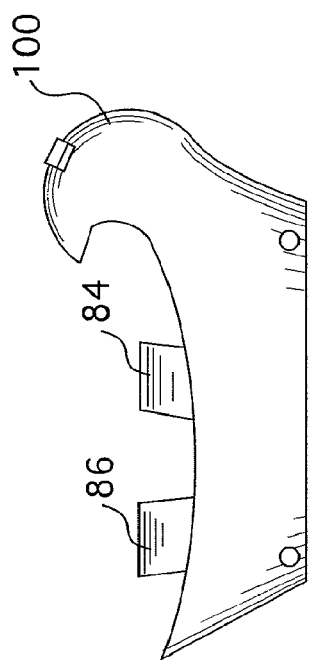
FIG. 9 is a right-side elevational view of the massager of FIG. 8.
Figure 7:
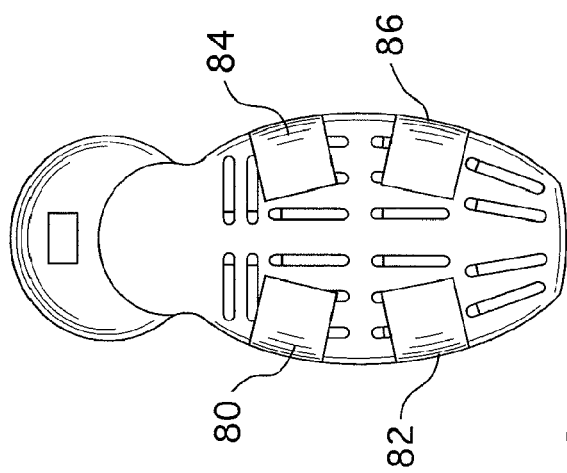
FIG. 7 is a top plan view of the infant massager of FIGS. 4-6 in the closed position.
Figure 8:
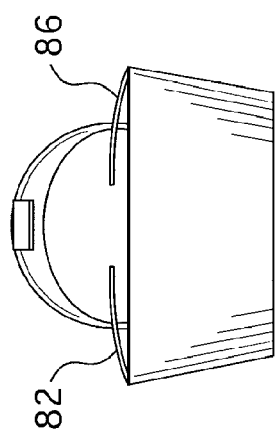
FIG. 8 is a front elevational view of the infant massager of FIG. 7.

FIGS. 7 through 9 show the massaging device of FIGS. 4 through 6 in the closed position.

FIG. 10 schematically illustrates a first massaging element 120 and a second massaging element 122 each being on four wheels 124, 126, 128 with the fourth wheel of massaging element 120 not being shown and with solely wheel 130 of massaging element 122 being shown. They are confined by a plurality of tracks 140, 142, 144, 146 and reciprocate in the indicated movement directions (Arrows A and B). It is noted that the upper surfaces of massaging elements 120, 122 are irregular and undulate so as to permit efficient massaging movement as the massaging element moves along the patient in paths parallel to each other.

Figure 11:
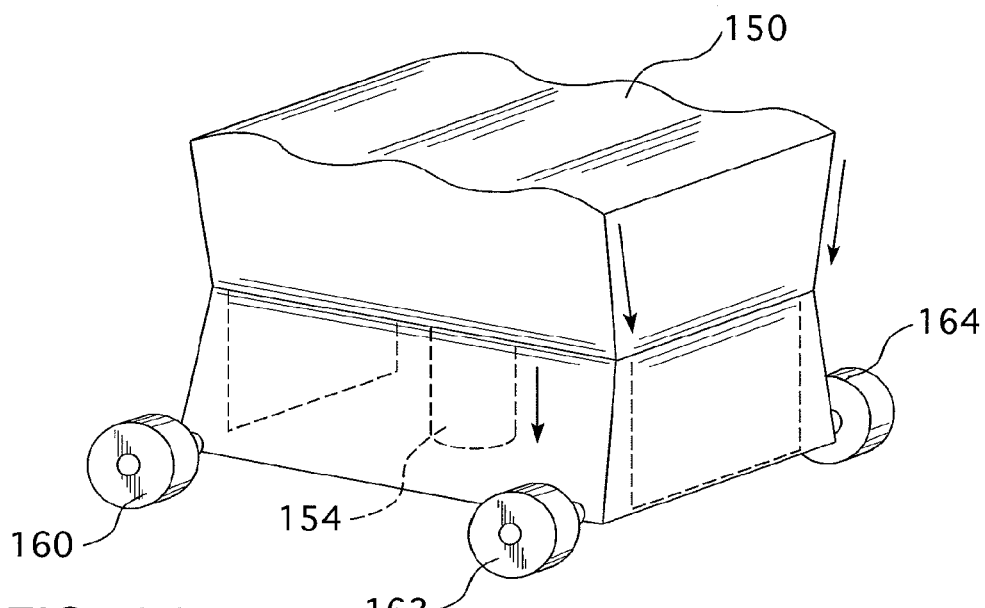
FIGS. 11 and 12 show in perspective, respectively, a massaging element of the present invention in the expanded and contracted positions.
Figure 12:
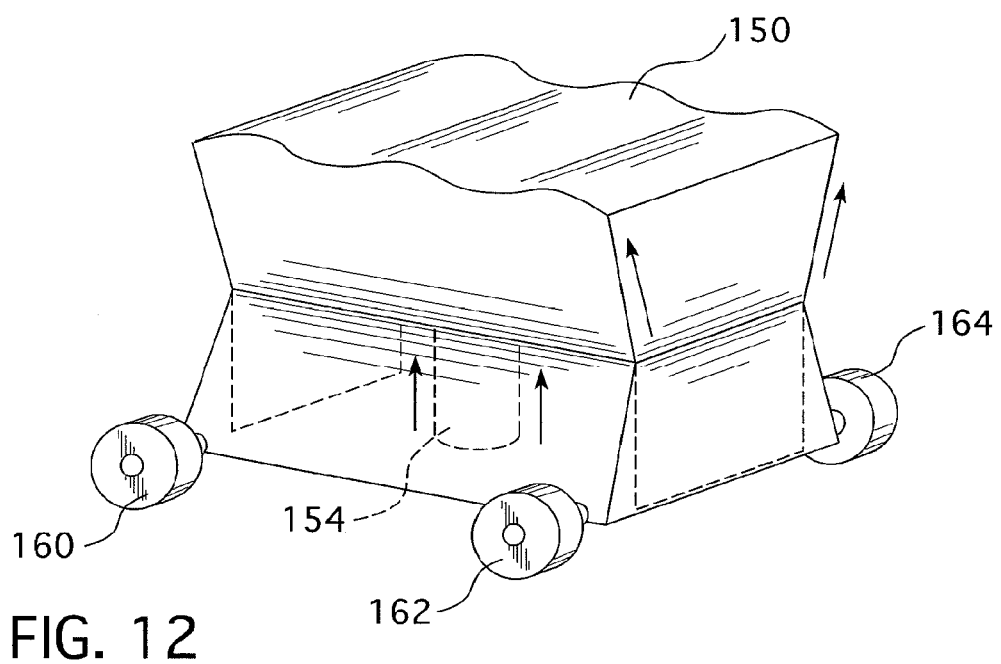

FIGS. 11 and 12 show, respectively, a massaging element in an extended position and in a contracted position. This permits variations in the intensity of the massage. This may be accomplished by any desired means, such as a rod or a piston 154 axially reciprocating in a vertical direction while engaged with the undersurface of the upper portion 150. It will be appreciated that the two pairs of wheels 160, 162, 164 (only three shown in FIGS. 11 and 12) may be restrained for the desired reciprocating movement by having upwardly-open grooves in the upper portions of tracks 140, 142, 144, 146 of FIG. 10.

Figure 13:
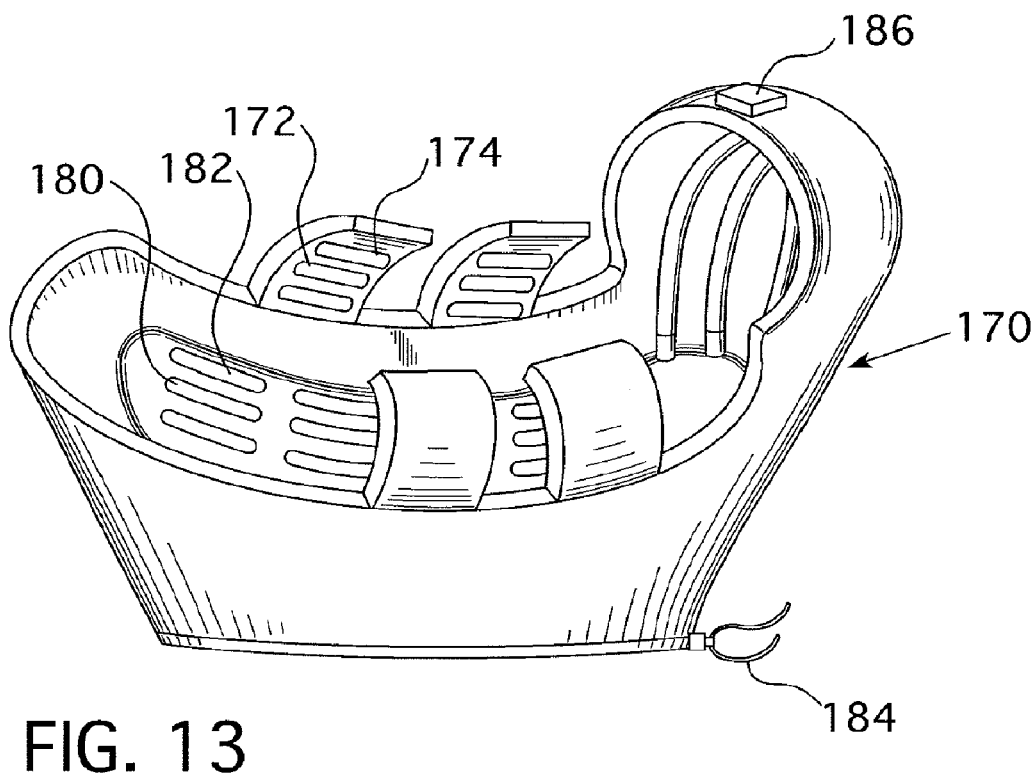
FIG. 13 is a form of cover for the infant massager of the present invention.

FIG. 13 shows a disposable cover 170 for the infant massager, which in each location, has slots, such as 172, 174, 180, 182, for passage of the individual massaging elements therethrough. An opening 186 for the brow monitor is provided. A tightening device, such as a tie string 184, may be provided to secure the cover to the massaging element.

Figure 13A:
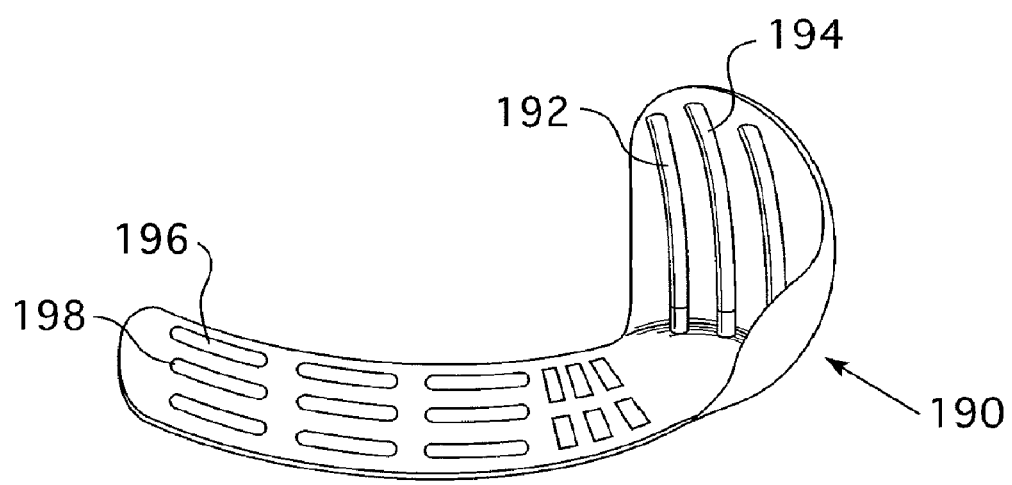
FIG. 13(a) is an alternate form of cover for the infant massager of the present invention.

FIG. 13(a) shows an alternate form of cover 190 which has a plurality of openings, such as 192, 194, 196, 198, for passage of the massaging elements therethrough.

Figure 14:
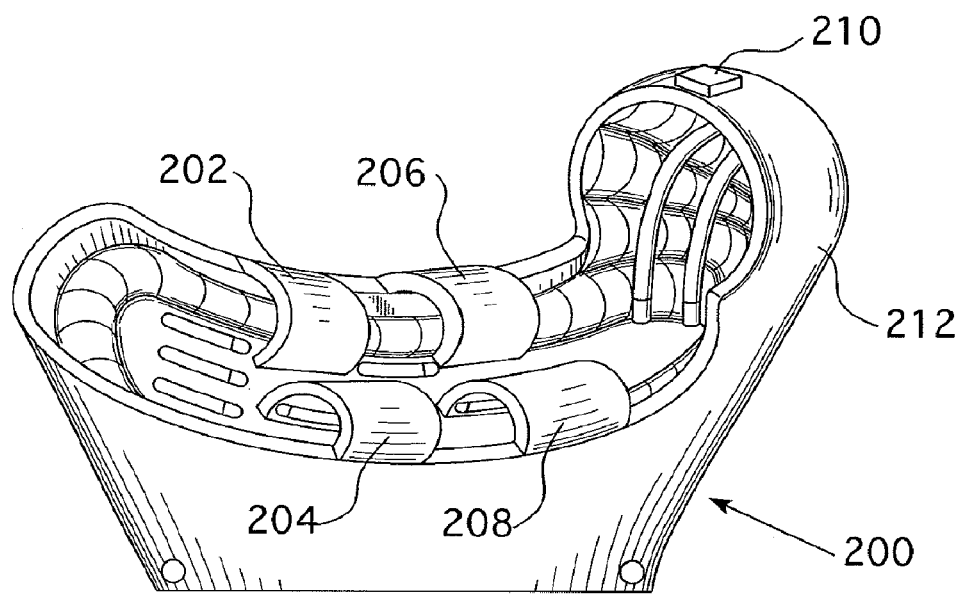
FIG. 14 is a perspective view of the infant massager of the present invention in the closed position.

FIG. 14 shows a perspective view of the infant massager 200 in the closed position with the arrays of leg massagers 202, 204 bent inward and an array of arm massagers 206, 208 folded inward. The brow monitor 210 is secured to the head support 212.

Referring to FIGS. 15 and 16, there is shown a version of the infant massager which has the arrays of movable massage elements, such as 220, 222, 224, 226, 228, 230, for example, and a padded border 230 around the interior, so as to protect the infant. In addition, there is a rotatable cover 240, which is structured to be in an up position as shown in FIG. 15, and in a lower position partially covering the feet and legs of the infant.

The exterior of the massaging unit will contain outlet/input slots for connecting other accessories and monitoring devices.

FIG. 16 shows a remote wireless controller 244 which is structured to have two-way communication with a transmitter (not shown) operatively associated with and preferably secured to the infant massager. The controller has a plurality of control buttons 246, 248, 250, 252, a display window for displaying data, facilitating control messages, and transmitting of the same. The display window 256 can also be structured to view the infant real time. An antenna 260 is integrally formed and projects from the remote receiver transmitter. A light 262 is structured to illuminate either in solid form or flashing form when an alarm condition exists or other attention-giving messages are desired. The remote receiver transmitter 244 can serve to turn the massage unit on, turn it off, program the transmitter operatively associated and preferably physically attached to the infant massager as to cycles of operation, and coordinate the receipt of emergency messages, such as undesired shutdown. It will be appreciated that while four control buttons 246, 248, 250, 252 are shown in FIG. 16, any number of desired control buttons may be employed.

The massaging unit will adjust the massage based on feedback from the internal monitoring sensors/equipment.

Figure 18:
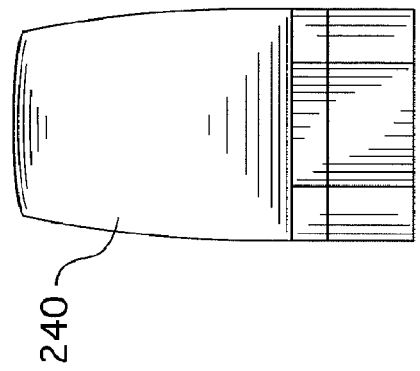
FIG. 18 is a front elevational view of the massager of FIG. 17.
Figure 19:
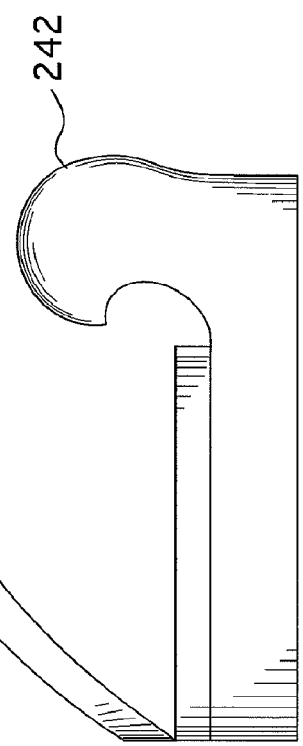
FIG. 19 is a right-side elevational view of the infant massager of FIG. 17.
Figure 17:
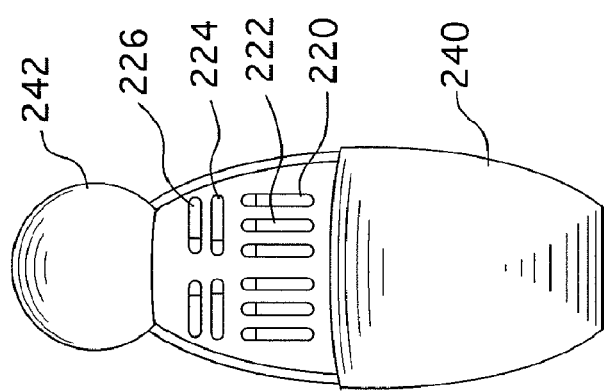
FIG. 17 is a top plan view of a full-term infant form of infant massager of the present invention.

FIGS. 17 through 19 show, respectively, a top view, front elevational view, and right-side elevational view of the massage unit of FIG. 15 with the cover 240, bead support 242, and arrays of massaging elements 220, 222, 224, 226, for example.

Figure 20:
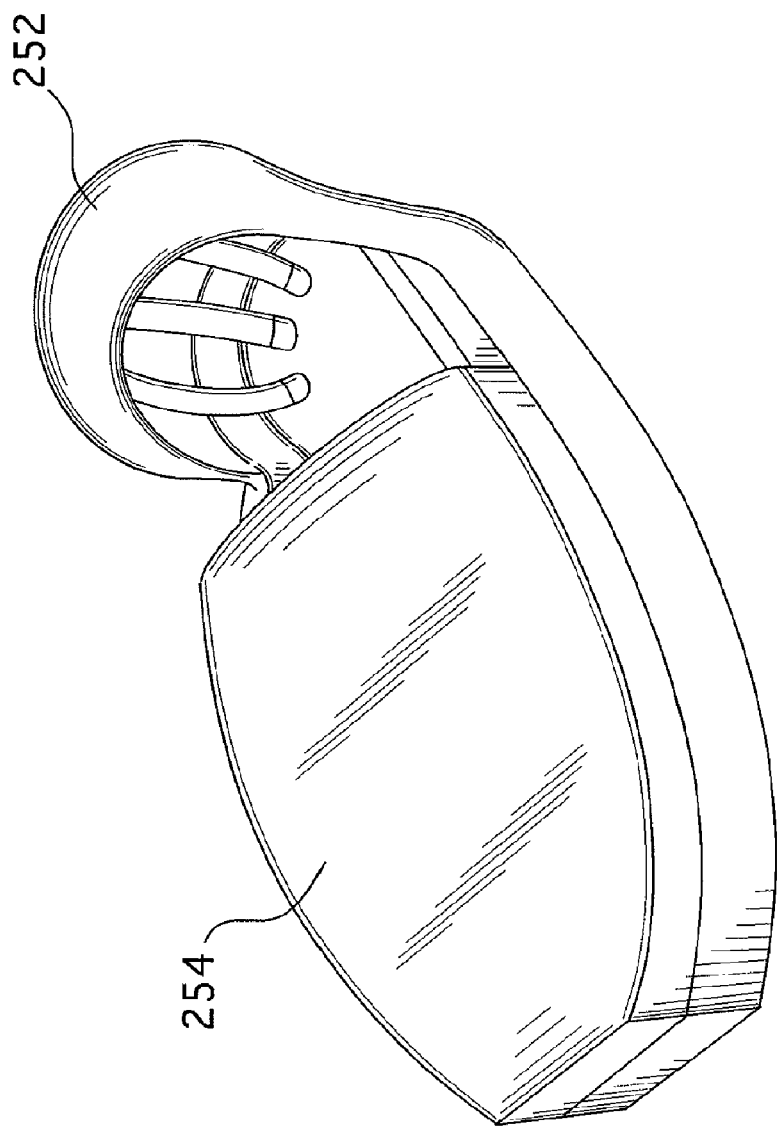
FIG. 20 is a perspective view of the closed-position massager of FIGS. 17 through 19.
Figure 21:
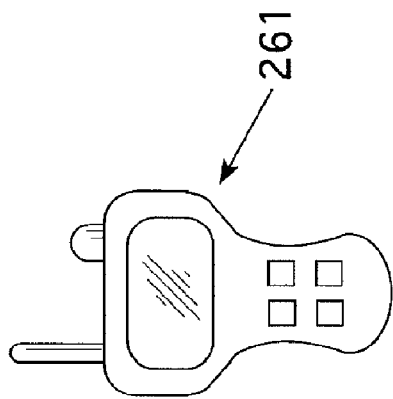
FIG. 21 is a remote wireless transmitter for controlling the operation of the infant massager of the present invention.

FIG. 20 shows a unit having an adjustable head support 252 and a cover 254 which is structured to cover the infant's chest, legs, and arms. An alternate embodiment would have a sheet that is placed inside the massager that is not fitted to cover the whole massage unit. An associated remote receiver transmitter 260 is shown in FIG. 21.

The massaging device can be used in an incubator, a radiant warmer, or on a table. The massaging device massages premature infants to help improve their health and help them gain weight. A disposable cover design that closely fits the geometry of the premature infant massager is provided to maintain the sterility of the massager.

The massaging device may integrate with neonatal intensive care unit ("NICU") monitoring equipment. The massaging device may automatically adjust the intensity of the massage based on a feedback system that relies on the behavioral and physical responses input. The massaging device may automatically shut off for potential safety problems or negative feedback from the baby.

In one embodiment, a disposable cover should be made of a soft, flexible material. The disposable cover should be a very soft material that does not irritate the infant's skin.

Figure 23:
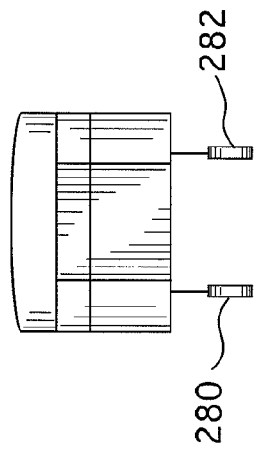
FIG. 23 is a front elevational view of the infant massager of FIG. 22.
Figure 24:
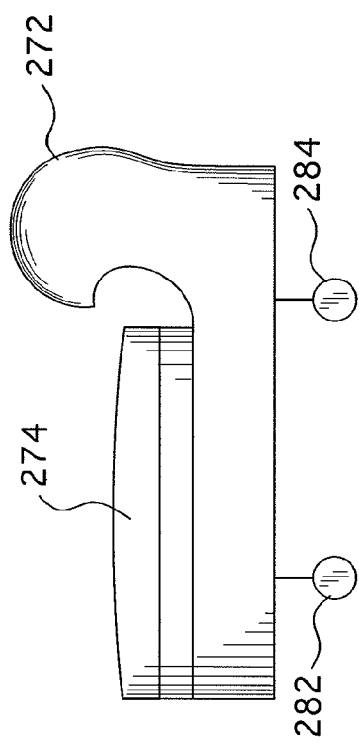
FIG. 24 is a right-side elevational view of the infant massager of FIG. 22.
Figure 22:
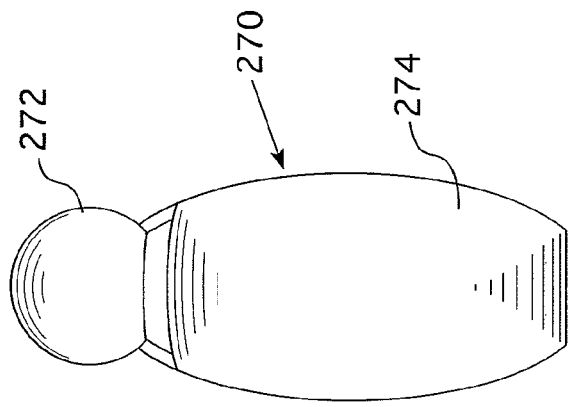
FIG. 22 is a top plan view of a form of infant massager of the present invention.

The embodiments of FIGS. 22 through 24 show, respectively, a top plan view of an infant massager 270 having a head support 272 and a cover 274 with four depending wheels 280, 282, 284 (only three are shown) to facilitate movement of the unit.

The remote receiver transmitter is a handheld device, which embodies a display screen. It will use wireless communication to communicate with the massaging unit. The remote receiver transmitter will be able to vibrate and sound an alarm when it is necessary to alert the user. The remote receiver transmitter contains a pointer pen (FIGS. 25 and 26) that the user can use to enter information into the device. The controller will contain a key pad to facilitate entering information or commands. It will contain a manual stop and start feature. It will also give the user the option to monitor the battery usage (premature infants). The remote receiver transmitter will contain buttons with different features pertinent to the massaging device's function.

The remote receiver transmitter will have an alarm mode where light illuminates or flashes at the top. It may contain a pointer pen that the user can use to enter information into the device.

For both premature infants and full-term infants, the portable remote receiver transmitter will have a key pad or pointer pen to enter information. It will contain a means of alerting the parents or other users of any safety features, mechanical problems, and shut-off. It will also contain the controls to adjust the video camera of the massaged baby. It will contain a screen where video of the baby can be viewed. It will also allow a parent or other user to select additional commands.

The control mechanism associated with the device and message adjustment/features could be placed on the massaging unit.

The massaging device may also be accompanied by a user's kit. The kit will contain all accessories needed to facilitate and/or enhance the massage. It will also contain any directions to set up the massaging system and the infant for the massage.

Examples of items the kit could contain: (a) the disposable cover; (b) brow monitor (similar to a baby forehead thermometer except it detects displacement); (c) massage oil and (d) connection to the vital signs monitor.

For full-term infants, a massaging kit would contain massage oil and a disposable cover. The items in the kit might not be sold as a kit, but as individual items.

The massage unit support surface preferably should be hard and covered with a soft material, such as plastic, for example. It can be made out of any materials that meets the user requirements, such as metal or plastic, for example. It should be able to facilitate being wiped and sterilized.

The massaging elements should be made hard and strong. These could be made out of appropriate materials that meet the requirements of the device. They should be covered by a flexible, wipeable material. It should be able to facilitate being wiped and sterilized.

The track/pulley/conveyor belt system could be made of a material that is strong, yet lightweight. The materials are preferably wipeable and easy to sterilize using conventional sterilizing techniques.

Figure 25:
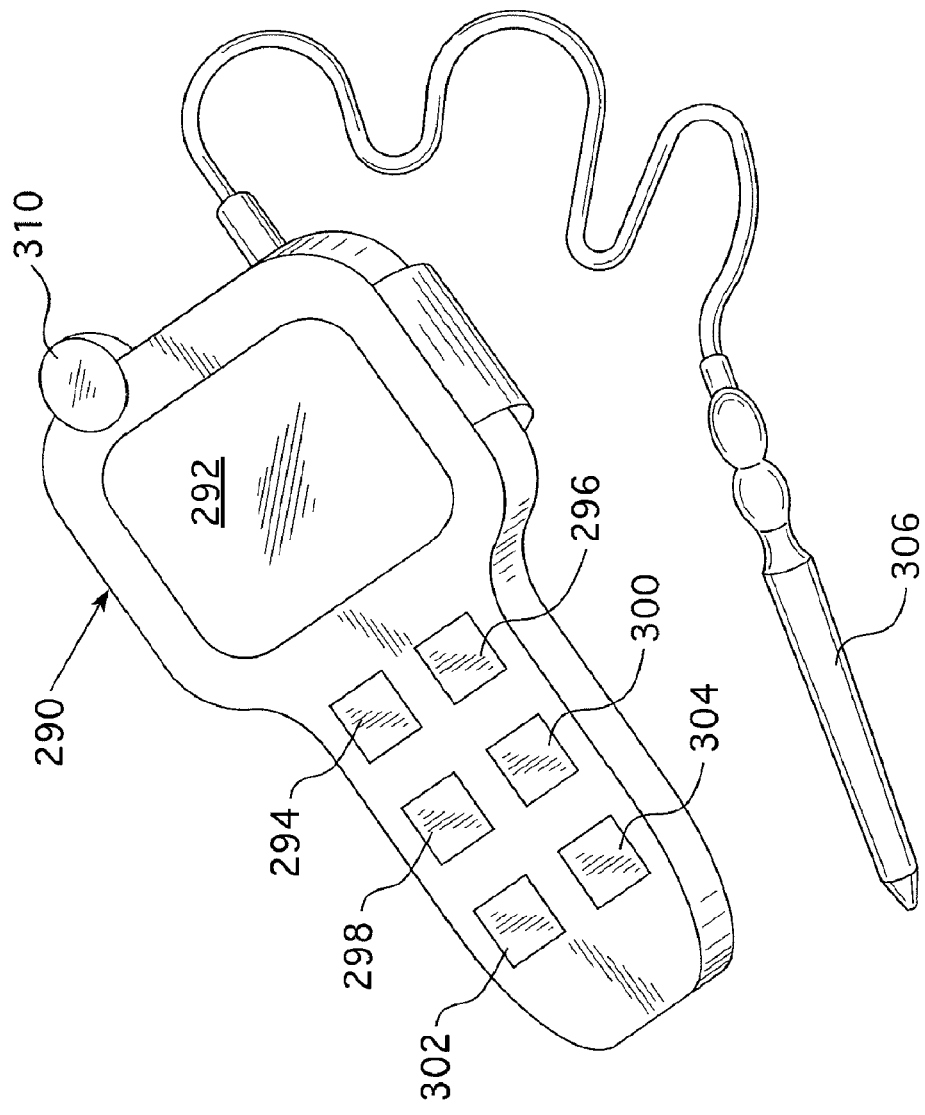
FIG. 25 is a perspective view of a form of remote receiver transmitter employable with an infant massager of the present invention with the pointer pen in the operating position.
Figure 26:
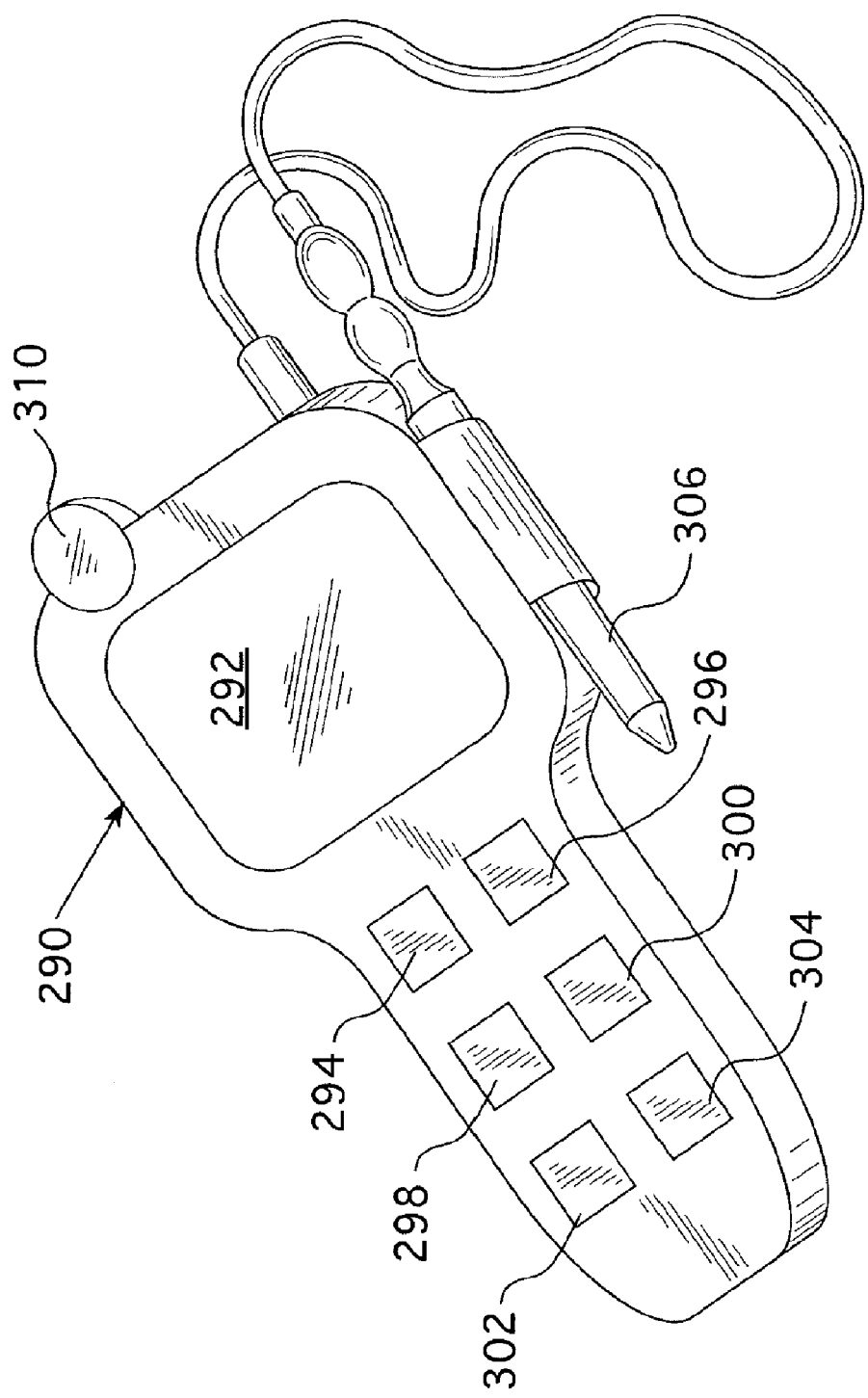
FIG. 26 is a perspective view of a form of transmitter for operating the infant massager with the pointer pen in the storage position.

FIGS. 25 and 26 illustrate a remote transmitter receiver or base station 290 having a display screen 292, control buttons 294, 296 for on/off controls, and additional controls 298, 300, 302, 304 with a pointer pen 306. A light 310 is provided and may be illuminated in solid form or blinking form and may be used as an emergency alarm indicator. Also, an audible alarm (not shown) secured to and operatively associated with the infant massager may be provided thereon, as well as on the remote receiver transmitter. The remote transmitter or base station 290 is structured to have wireless communication with a receiver transmitter operatively associated with and preferably on the massager unit.

The remote receiver transmitter for the infant massager allows the user to both receive and input information about the massager and the infant. This may include: (i) notifying the user of "power off" through sounds, lights, or vibrations, (ii) monitoring of power supply, (iii) allowing a user to manually stop and start the device, (iv) allowing the user to select intensity of massage, (v) optimizing/coordinating the usage of the device among the premature infants in a NICU unit, (vi) allowing the user to select the monitored physical parameters of the infant, (vii) allowing the user to get a printed summary of the infant's behavior and vitals changes at the end of the massage, (viii) alerting the user to when the device needs to be recharged, and (ix) alerting/informing the user about any safety problem or mechanical failures. The massager may adjust the massage based on feedback from internal and external monitoring equipment.

The massaging device for infants can be aimed at improving overall developmental skills, sleep, colic, and overall health of the infant. The massaging device will adjust the massage based on behavioral and physical feedback. The massaging device will preferably massage the front and back of the body including the arms, legs, back, and head. The massaging device also includes features to enhance sleeping and comfort. The massaging device can provide video of the infant being massaged.

The massage device may contain safety features that cause the device to turn off automatically.

The massage device will contain a remote receiver transmitter that may:

(a) allow the user to adjust the massage setting;
(b) allow the user to view video of the infant during the massage;
(c) contain mechanisms to alert users when the device has stopped;
(d) contain mechanisms to alert the user to mechanical problems/failures; and
(e) allow the user to manually stop or start the massage.

The massage device has a lid that has adjustable height features.

The massage device maintains massaging elements in contact with the body and adjusts massage to maintain appropriate pressure.

Figure 27:
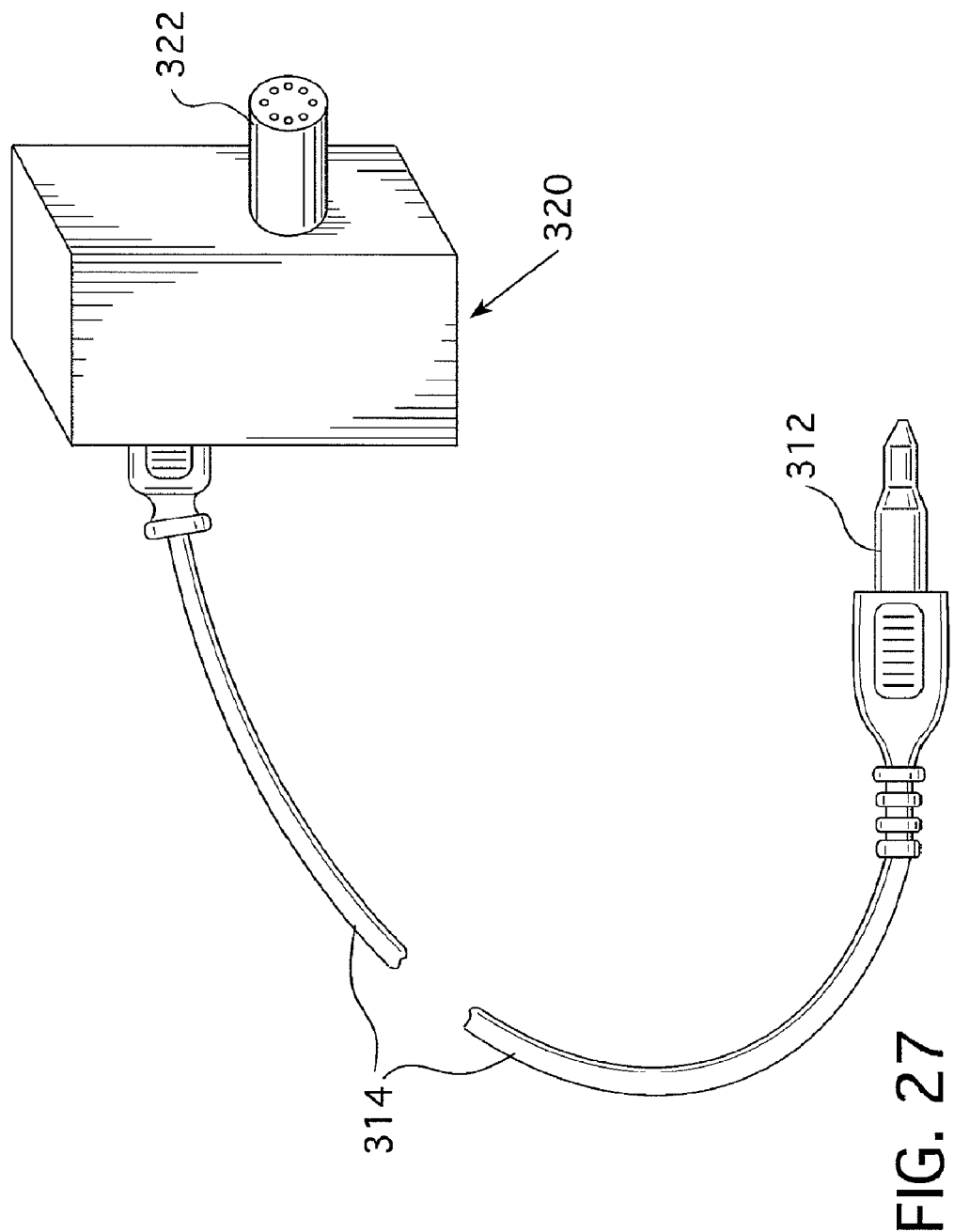
FIG. 27 is a schematic view of an accessory for monitoring cardio-respiration of the infant.

FIG. 27 illustrates a jack 312 which plugs into the infant massager, and by a suitable electrical lead 314, is connected to the massager and is operatively associated with a microprocessor, which is part of the massager. It is adapted to cooperate with the transmitter which is part of the massager, to transmit information to the remote receiver. This serves to facilitate monitoring of the infant's cardio output and respiratory rate. The connection 322 is to the cardio-respiratory monitor and receives information which is preliminarily processed in microprocessor unit 320 with the output passing over lead 314 through the jack 312 into the microprocessor. In this fashion, departures from the desired cardio/respiratory values or confirmation that they remain within the desired range may be transmitted remotely to the handheld unit or other receiver.

Figure 28:
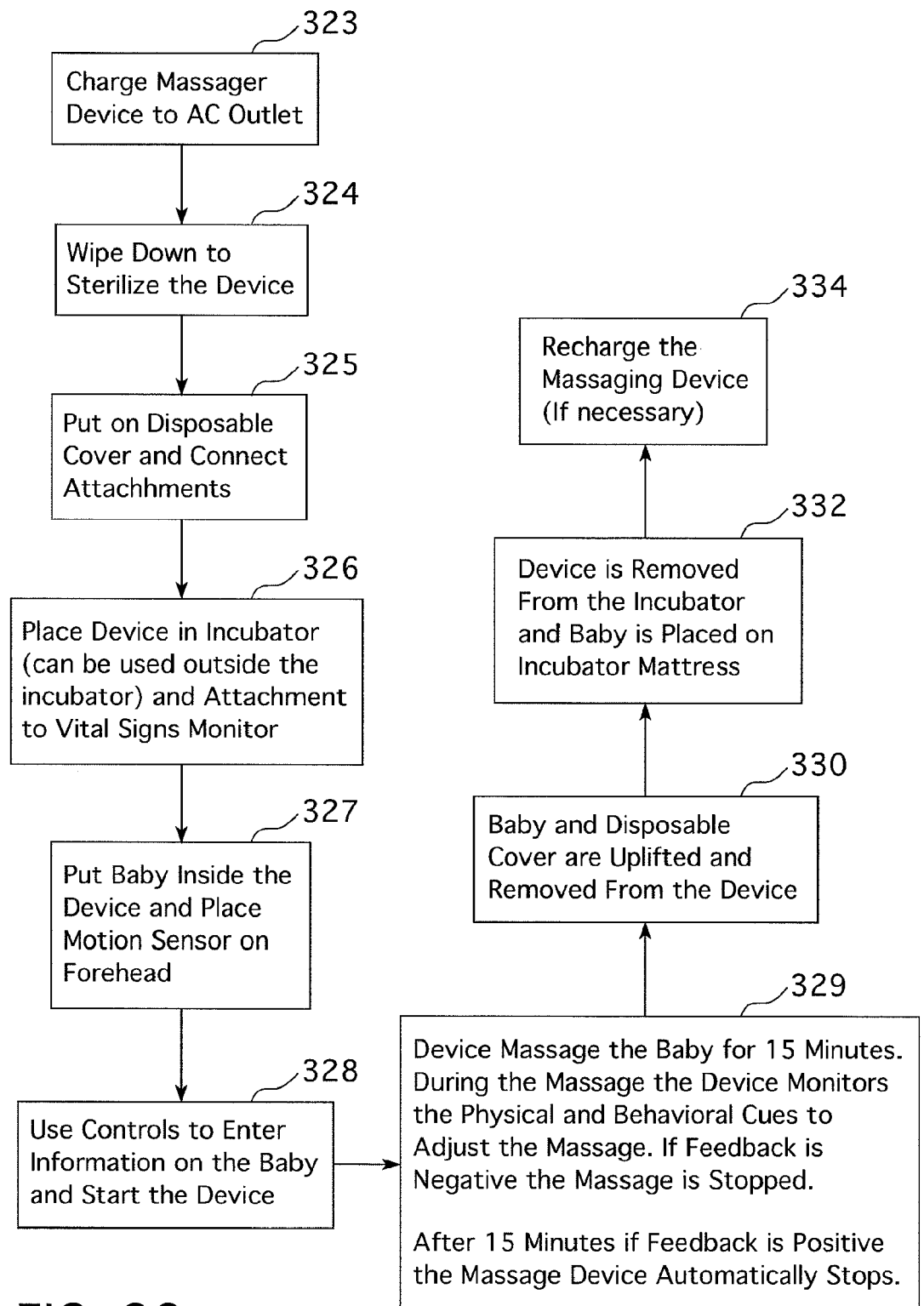
FIG. 28 is a flow diagram showing operation of an infant massager of the present invention on a premature infant.
Figure 29:
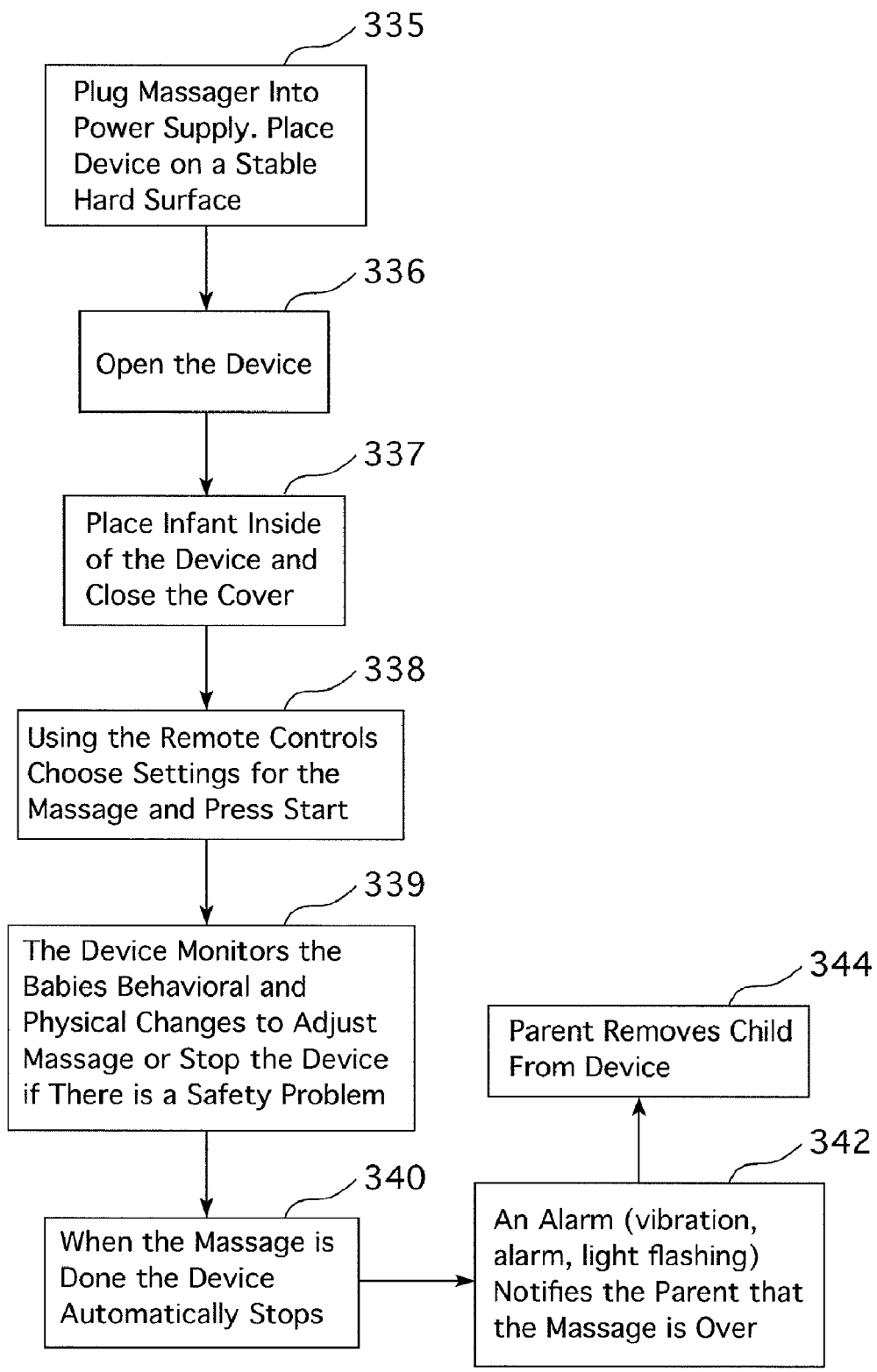
FIG. 29 is a schematic view showing a sequence of operation of an infant massager for full-term infants.

FIGS. 28 and 29 disclose, in a block diagram, a sequence of operation, respectively, for premature infants and full-term infants. Referring in greater detail to FIG. 28 and the use of the system for premature infants, the unit is first charged in an AC outlet 323 and is then wiped down to sterilize the device 324. A disposable cover and connect attachments are then placed in position 325. The device is placed in an incubator or can be employed outside the incubator or attachment to a vital signs monitor 326. The infant is then placed inside the device, and a motion sensor is placed on the forehead 327. Controls are employed to enter information on the infant and start the device 328. The device massages an infant for fifteen minutes, and during the massage, the device monitors the physical and behavioral changes in order to adjust the massage. If the feedback is negative, the massage is stopped. After fifteen minutes, if the feedback is positive, the massage device automatically stops 329. The infant and the disposable cover are lifted and removed from the device 330 after which the device is removed from the incubator, and the infant is placed on the incubator mattress 332. The massaging device is then recharged if it is in need of such charging 334.

Referring to FIG. 29, use of the massager on a full-term infant will be considered. The massager is first plugged into a power supply and placed on a stable, hard surface 335 after which the device is opened 336. The infant is placed inside the device, and the cover is closed 337. Employing remote receiver transmitters, settings for the massage are established, and the start button is pressed 338. The device monitors the infant's behavior and physical changes to adjust the massage or stop the device if there is a safety problem 339 after which when the massage is completed, the device stops automatically 340. An alarm, which may be a vibration, an audible alarm, or a flashing light, notifies the user that the massage is over 342 after which the user removes the infant from the device 344.

The massaging unit for a full-term infant contains a housing which massages all parts of the body. The housing unit for the massage device will have a cover that will secure the infant in the device. The lid of the device is attached to an adjustable support which will allow the lid 240 to be lowered into contact with the infant's skin. The unit will preferably also include a support surface where the infant will be placed. The support surface will be covered with soft materials and will have boundaries where needed.

The massaging elements of the device will protrude from open slots on the support surface and from the underside of the lid of the massaging device. The slots for the massaging elements will be arranged in parallel, horizontal, and/or vertical rows. The massaging elements will be enclosed by a thin, flexible, expandable material.

The massaging elements may consist of a rectangle-shaped piece with a modulated/wavy top surface (the surface that comes in contact with the skin). The massaging element will be secured to a track system or a conveyor belt system that will rotate to move the massaging elements in reciprocating movements. The massaging elements will move in reciprocating movements sequentially by body part. All massaging elements located in the same region of the body will move in the same reciprocating movement simultaneously.

It will be appreciated that various means well-known to those skilled in the art will be employed to effect the desired reciprocating movement of the massage elements. For example, a linear actuator of the electro-mechanical variety may be employed with the linear movement from the output of a single motor employed to reciprocate a single massage element or a plurality of elements. Alternatively, rack and pinion means may be employed with the rack being secured to the underside of a massage element and the pinion engaged therewith driven in rotary fashion by the output shaft of the motor with or without an intervening speed adjusting gear box. Another approach would be to have the massage elements secured to a conveyor. The advantageous use of a motor which reverses direction or a linkage which effects reciprocation may be employed.

Figure 30:
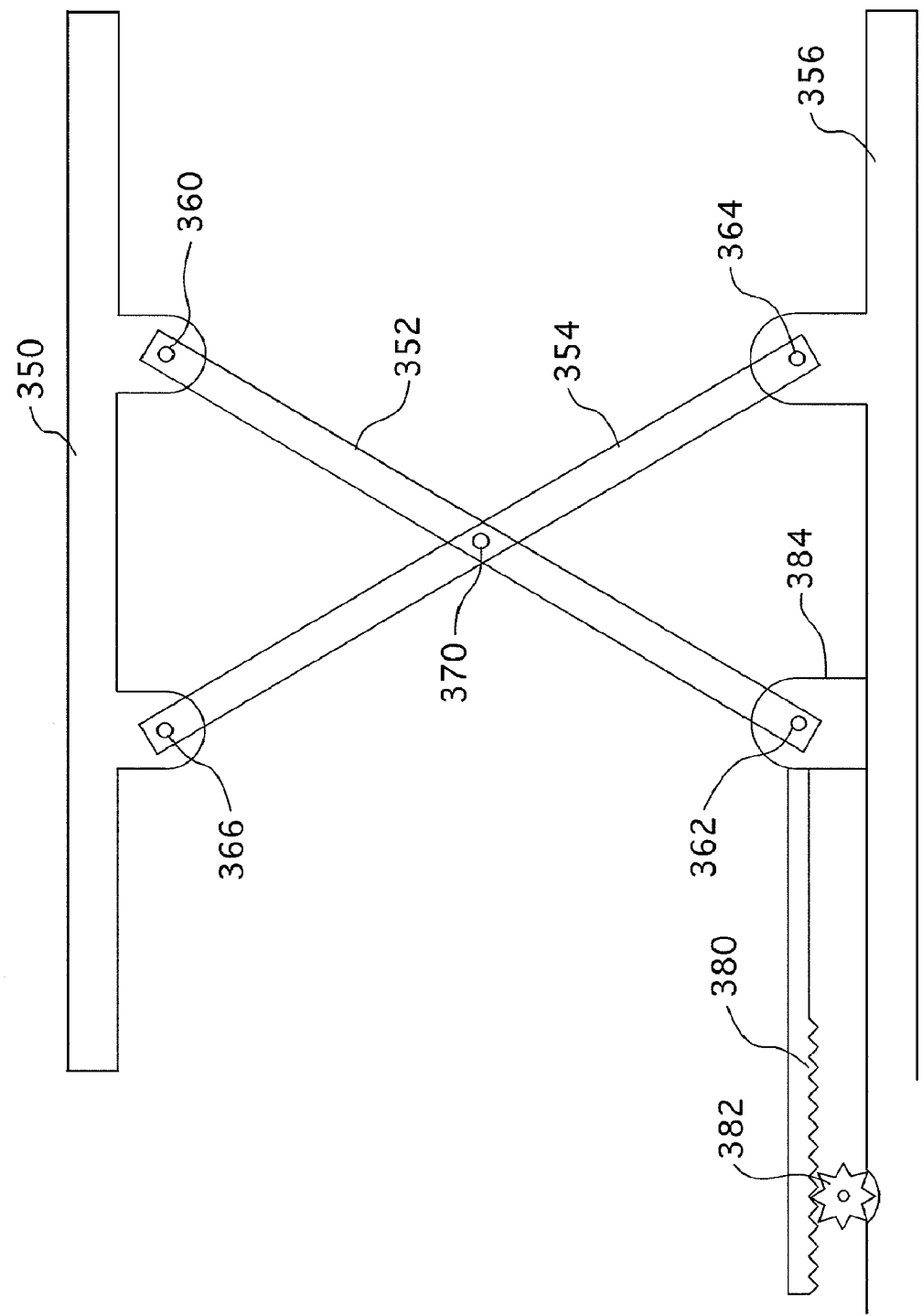
FIG. 30 is a schematic view of apparatus usable to raise and lower a massage element.

Referring to FIG. 30, there is shown a way of elevating and reducing the level of the upper portion of a massaging element. The upper platform 350, which will support the massaging element upper part, has pivotal linkage to links 352, 354. Link 354 pivots about pivots 364, 366, the former of which is connected to base 356. Link 352 pivots about 360, 362 with pivot 370 serving to connect pivotally the two links 352, 354. Rack 380 is secured to element 384 which is slidably secured to base 356. Output of the motor (not shown) functions to rotate pinion 382 which is engaged with rack 380. It will be appreciated that rotation of pinion 380 causes lateral movement to the right or left of rack 380 and responsive movement to linkage of platform 350 upwardly or downwardly, thereby adjusting the height of the massage element.

The massaging elements 6, 90, 92, 104, 106, etc. of the device will protrude from open slots on the support surface and from the under-surface of the arm and leg massage protrusion. The slots for the massaging elements will be arranged in parallel, horizontal, and/or vertical rows. The massaging elements will be enclosed by a thin, expandable material. In the alternative, the massager may be made of a resilient material which preferably is cleanable so as to facilitate cleaning with an appropriate solution or even sterilization.

The inside of the housing unit will contain a rechargeable battery which could be used to power the motors needed to move the track or conveyor belt, the track or conveyor belt system, and the massaging elements. The exterior of the massaging unit will contain outlet/input slots to connect to vital signs monitor or other monitoring accessories to the device.

It will be appreciated that the reciprocating massaging elements are secured to the infant massager in such a way as to resist separation, but permit the desired reciprocating movement.

While the preferred approach of having several groupings of pluralities of reciprocating massaging elements has been shown, it will be appreciated that variations in the number and orientation of such elements may be employed if desired.

In a preferred approach to the invention, as illustrated, an upwardly open recess for receipt of an infant will be provided. Particularly with respect to premature infants, it is preferred that the contour of the massager be curved so as to create a generally concave, upwardly facing configuration to facilitate the infant being held in such a position.

Among additional features, which can be provided in the massager:

(a) The massaging device fits inside can be used in an incubator, a radiant warmer or on a table.

(b) The massaging device massages premature infants to help improve their health and help them gain weight.

(c) A disposable cover design closely fits the geometry of the premature infant massager to maintain the sterility of the massager.

(d) A massaging device integrates with NICU monitoring equipment.

(e) A massaging device automatically adjusts the intensity of the massage based on a feedback system that relies on the behavioral and physical responses input.

(f) A massaging device automatically shuts off for potential safety problems or negative feedback from the baby.

While, for simplicity of disclosure, the remote receiver transmitter has been shown as a wireless unit, it may, if desired, be connected to the massager through a wired connection. The system will have a microprocessor for receiving information from the massage unit and delivering information thereto and to the remote receiver transmitter. The remote receiver transmitter may function as a base station. The microprocessor may be a separate unit or may be part of the remote receiver transmitter or part of a separate base station. Among the functions of the microprocessor will be the receipt of information from the receiver transmitter of the massager, process the same, and send control signals to the remote receiver transmitter, which in turn, will send signals to the receiver transmitter. The microprocessor may also receive and process information from a cardio-respiration monitor which is monitoring the infant.

EXAMPLE

An example of operation of the massager will be considered. Before using the device, it should be charged by plugging into a wall outlet or energized by plugging it into a wall outlet. The massager will then be wiped down with a disinfecting cloth to clean the massaging surface. The disposable cover will be fitted to the massager with the arms and legs massagers in the open position (see FIG. 1). A small forehead motion sensor will be connected to the device. The device will be placed inside the incubator (or on table's surface) and will be connected to cardio-respirator monitor. The infant will be placed inside the massager. The forehead motion sensor will be placed on the infant's skin over the brow. The user will then use the handheld system control unit to:

(a) enter the infant's name, gestational age, and weight;
(b) choose the intensity of the massage;
(c) choose the length of the massage, such as five or ten minutes, for example;
(d) start the massage.

The device will preferably not start until information on gestational age and weight has been entered. The massager will continuously monitor the infant once activated to adjust the massage or turn off the device if the infant is showing signs of distress.

Once the settings have been chosen, the device will be activated to move the arms and legs massager elements, which are in the open position, and slowly curl down until the massager elements are in contact with the infant's skin. All massaging parts will adjust as necessary to administer the specified intensity of massage based on the infant's weight.

The device will start by massaging the infant in the following sequence massaging each area for roughly one minute (total time of five minutes):

(a) head;
(b) upper shoulders and arms;
(c) back (from upper shoulders to lower back);
(d) arms (from shoulders to wrist); and
(e) legs (upper thighs to ankle).

The massager will rest for three minutes between massaging sessions. If a ten-minute massage session has been chosen, two five-minute massages will be given. If a fifteen-minute massage session has been chosen, three five-minute massage sessions will be administered with two three-minute breaks between sessions. During the massage session, the nurse will be able to use the handheld control system to monitor the infant's response to the massage by pressing infant response button. When the massage is completed, the massager will automatically turn off. An alarm on the handheld control system will sound an alarm, vibrate, and blink a flashing blue light to inform the nurse that the device has been turned off. If the device automatically shuts off for any reason other than the completion of a massaging session, a different light color (a red light) will flash along simultaneously with the vibrations to alert the nurse to any possible problems with the baby or the device.

Whereas particular embodiments of the invention have been described herein for purposes of illustration, it will be evident to those skilled in the art that numerous variations of the details may be made without departing from the invention as set forth in the appended claims.

The invention claimed is:

1. An automated infant massager comprising:
a base for supporting said infant,
a plurality of first movable massage elements structured to underlie at least a portion of said infant,
at least one motor for effecting reciprocating movement of said first movable massage elements with respect to said infant,
said first movable massage elements being structured to massage at least a portion of said infant's back,
a plurality of second movable massage elements being structured to massage at other portions of said infant,
said automated infant massager structured to automatically monitor physical and behavioral changes of said infant, and
said automated infant massager having a microprocessor for receiving information from monitoring sensors of said infant massager regarding said monitored physical and behavioral changes of said infant, processing the same, and emitting signals with respect thereto to said infant massager when it is performing said massage to adjust or shut off said infant massager.

2. The infant massager of claim 1 including
said plurality of second movable massage elements being structured to massage at least portions of said infant's arms and legs.

3. The infant massager of claim 2 including
said second movable massage elements having one group of said movable massage elements for massaging a first arm and a first leg and another group of said movable massage elements for massaging a second arm and a second leg.

4. The infant massager of claim 1 including said infant massager having an infant's head support.

5. The infant massager of claim 4 including
a plurality of third movable massage elements structured to be subjected to translational movement and being secured to said head support and structured to massage at least a portion of said infant's head.

6. The infant massager of claim 1 including
said infant massager structured to accommodate a premature infant.

7. The infant massager of claim 1 including
said infant massager structured to accommodate a full-term infant.

8. The infant massager of claim 1 including
a majority of said first movable massage elements being structured to reciprocate in a direction generally parallel to the other said first movable massage elements.

9. The infant massager of claim 8 including
said first movable massage elements reciprocating in a path generally parallel to the spinal column of said infant.

10. The infant massager of claim 1 including
said at least one motor energized by at least one battery.

11. The infant massager of claim 1 including
said at least one motor energized from an electrical outlet.

12. The infant massager of claim 1 including
employing a plurality of motors to reciprocate said first movable massage elements.

13. The infant massager of claim 1 including
a plurality of fourth movable massage elements structured to underlie the shoulders of said infant and establish reciprocating movement thereof in a path generally perpendicular to the orientation of the spinal column of said infant.

14. The infant massager of claim 1 including
said first movable massage elements having an undulating massaging surface structured to contact said infant.
15. The infant massager of claim 2 including
said plurality of second movable massage elements being mounted on movable supports which are structured (a) through rotation, assume an open position not in contact with said infant to facilitate introduction of said infant into and withdrawal of said infant out of said infant massager and (b) through rotation, a closed position with said second movable massage elements in contact with said infant.
16. The infant massager of claim 1 including
a brow monitor for providing an output indication of infant discomfort.
17. The infant massager of claim 16 including
said output being capable of initiating an alarm selected from the group consisting of a vibration, a visual alarm, and an audible alarm.
18. The infant massager of claim 1 including
said infant massager having a timer structured to turn the massager off after a predetermined time interval.
19. The infant massager of claim 1 including
said infant massager having a timer structured to turn on the massager at a predetermined time.
20. The infant massager of claim 1 including
said plurality of first movable massage elements structured to assume a first expanded position and a second compressed position, and
said plurality of first movable massage elements structured to be movable in a reciprocating path in an expanded or contracted position.
21. The infant massager of claim 1 including
said at least one motor being operatively associated with said first movable massage elements by a mechanical transmission.
22. The infant massager of claim 21 including
said transmission including an endless belt and pulleys for delivering the output of said at least one motor to said first movable massage elements.
23. The infant massager of claim 21 including
said transmission including gearing for delivering the output of said at least one motor to said movable massage elements.
24. The infant massager of claim 1 including
a cover member structured to be interposed between at least some of said first movable massage elements and said infant.
25. The infant massager of claim 1 including
a cover member having openings for receiving at least some of said first movable massage elements.
26. The infant massager of claim 4 including
a brow monitor securable to an infant's forehead for monitoring brow movements.
27. The infant massager of claim 26 including
said massager having a microprocessor; and
said massage unit structured to transmit information to a remote receiver transmitter when brow movement of the infant has occurred and said microprocessor has determined that said infant is in distress.
28. The infant massager of claim 25 including
said cover member being disposable.
29. The infant massager of claim 1 including
said infant massager having a massage unit receiver transmitter for receiving signals from a remote receiver transmitter and transmitting signals thereto.
30. The infant massager of claim 29 including
said massager having a microprocessor operatively associated with said massage unit receiver transmitter.
31. The infant massager of claim 1 including
said microprocessor structured to receive information from a cardio-respiration monitor, process said information, and transmit processed information signals.
32. The infant massager of claim 31 including
said microprocessor structured to deliver said processed information signals to said remote receiver transmitter.
33. The infant massager of claim 1 including
at least one motor for effecting reciprocating movement of said second movable massage elements with respect to said infant.
34. The infant massager of claim 5 including at least one motor for effecting reciprocating movement of said third movable massage elements with respect to said infant.
35. The infant massager of claim 13 including at least one motor for effecting reciprocating movement of said fourth movable massage elements with respect to said infant.
36. The infant massager of claim 1 including
said microprocessor structured to emit said signals to a remote receiver transmitter.
37. The infant massager of claim 36 including
said remote receiver transmitter being structured to deliver control signals to other portions of said infant massager.
38. The infant massager of claim 1 including
said automated infant massager having a vital signs monitor.
39. The infant massager of claim 1 including
said infant supporting base having a generally upwardly-facing, concave configuration structured to receive said infant with said infant being in a generally horizontal position.
40. The infant massager of claim 1 including
said microprocessor responsive to said received information regarding monitored physical and behavioral changes structured to emit signals to adjust one of the intensity and duration of said massage.
41. The infant massager of claim 40 including
said remote receiver transmitter structured to receive said microprocessor-emitted signals and to responsively adjust said massage intensity.
42. The infant massager of claim 40 including
said remote receiver transmitter structured to receive said microprocessor-emitted signals and to responsively adjust the duration of said massage.
43. The infant massager of claim 42 including
said remote receiver transmitter structured to receive said microprocessor-emitted signals and to responsively automatically terminate said massage in the event that said microprocessor signals contain predetermined information selected from the group consisting of safety parameters and negative feedback related to physical or behavioral changes of said infant.
44. The infant massager of claim 16 including
said brow monitor secured to said head support.
45. The infant massager of claim 1 including
a video camera for providing images of said infant during operation of said massage to assist with monitoring the physical and behavioral changes of said infant.
46. The infant massager of claim 29 including
said remote receiver transmitter having a screen for displaying images of said infant.

47. The infant massager of claim 46 including
a video camera for providing images of said infant during operation of said massager to assist with monitoring the physical and behavioral changes of said infant.

48. The infant massager of claim 29 including
said remote receiver transmitter being structured to allow the user to input information.

49. The infant massager of claim 39 including
said infant supporting base having a padded border to protect said infant.

50. The infant massager of claim 1 including
said first movable massage elements being enclosed by a flexible material.

51. The infant massager of claim 29 including
said remote receiver transmitter structured to provide a user with information from said massage unit receiver transmitted signal.

52. The infant massager of claim 48 including
said remote receiver transmitter is structured to provide a plurality of the functions selected from the group consisting of (a) allow the user to adjust the massage setting;
(b) allow the user to view video of the infant during the massage;
(c) contain mechanisms to alert users when the device has stopped;
(d) contain mechanisms to alert the user to mechanical problems/failures;
(e) allow the user to manually stop or start the massage; and
(f) allow the user to enter information about the infant.

53. The infant massager of claim 27 including
said massager being structured to connect said microprocessor with a cardio-respirator monitor to provide input into said microprocessor regarding said infant's cardio output and respiratory rate.

54. The infant massager of claim 29 including
said remote receiver transmitter being a wireless receiver transmitter.

* * * * *

UNITED STATES PATENT AND TRADEMARK OFFICE
CERTIFICATE OF CORRECTION

| | | |
|---|---|---|
| PATENT NO. | : 8,142,375 B2 | Page 1 of 1 |
| APPLICATION NO. | : 12/051906 | |
| DATED | : March 27, 2012 | |
| INVENTOR(S) | : Sanna Gaspard | |

It is certified that error appears in the above-identified patent and that said Letters Patent is hereby corrected as shown below:

Figure 28, reference 325, line 3, "Attachhments" should read --Attachments--.
Figure 29, reference 339, line 2, "Babies" should read --Baby's--.
Column 2, line 62, "massager is suitable" should read --massager that is suitable--.
Column 3, line 34, "the and associated" should read --and associated--.
Column 6, line 1, "220, 222, 224, 226, 228, 230" should read --220, 222, 224, 226, 228--.
Column 6, line 41, "260" should read --261--.
Column 10, line 5, "pinion 380" should read --pinion 382--.
Column 10, line 41, "device fits" should read --device that fits--.

Signed and Sealed this
Twenty-sixth Day of June, 2012

David J. Kappos
*Director of the United States Patent and Trademark Office*